United States Patent [19]

Psarras et al.

[11] 4,032,566

[45] June 28, 1977

[54] OMEGA-CARBOMETHOXYPER-FLUOROALKYLENE OXIDE IODIDES

[75] Inventors: Theodore Psarras, Gainesville, Fla.; Christ Tamborski, Dayton, Ohio

[73] Assignee: The United States of America as represented by the Secretary of the Air Force, Washington, D.C.

[22] Filed: Sept. 4, 1975

[21] Appl. No.: 610,471

[52] U.S. Cl. .................. 260/484 R; 260/453 R; 260/465.2; 260/544 F; 260/561 HL; 260/615 BF

[51] Int. Cl.² ................................ C07C 69/66

[58] Field of Search ..................... 260/484 R

[56] References Cited

UNITED STATES PATENTS

| | | | |
|---|---|---|---|
| 2,713,593 | 7/1955 | Brice et al. | 260/484 R |
| 3,125,599 | 3/1964 | Warnell | 260/484 R |
| 3,646,112 | 2/1972 | Sterling, Jr. | 260/484 R |
| 3,657,306 | 4/1972 | Murray | 260/484 R |
| 3,674,800 | 7/1972 | Sweeney et al. | 260/484 R |
| 3,697,564 | 10/1972 | Anello et al. | 260/484 R |
| 3,847,978 | 11/1974 | Siamesi et al. | 260/484 R |

*Primary Examiner*—Paul J. Killos
*Attorney, Agent, or Firm*—Joseph E. Rusz; Cedric H. Kuhn

[57] ABSTRACT

Fluorinated ethers are provided that contain two functional end groups (ester and iodide groups) separated by a plurality of difluoromethylene, fluoro-trifluoromethylmethylene and oxygen groups. The compounds are useful as intermediates, particularly in the synthesis of fluoroalkylether difunctional compounds which can be used in the preparation of improved thermally stable polymers.

4 Claims, No Drawings

OMEGA-CARBOMETHOXYPERFLUOROALKYLENE OXIDE IODIDES

RIGHTS OF THE GOVERNMENT

The invention described herein may be manufactured and used by or for the Government of the United States for all governmental purposes without the payment of any royalty.

This invention relates to omega-carbomethoxyperfluoroalkylene oxide iodides. In one aspect it relates to a process for synthesizing the compounds.

BACKGROUND OF THE INVENTION

In U.S. Pat. No. 3,453,333, M. H. Litt et al. disclose fluorinated ethers containing at least one halogen substituent other than fluorine. Because this substituent provides a potential reactive site, the compounds can be used as intermediates in the synthesis of other compounds, particularly in the preparation of surfactants.

It is an object of this invention, therefore, to provide fluorinated ethers which have two reactive end groups.

Another object of the invention is to provide fluorinated ethers which are particularly useful as intermediates for synthesizing monomeric materials.

A further object of the invention is to provide a process for preparing the fluorinated ethers.

Other objects and advantages of the invention will become apparent to those skilled in the art upon consideration of the accompanying disclosure. The omega-carbomethoxyperfluoroalkylene oxide iodides are, for the sake of simplicity of expression, generally referred to herein as "fluorinated ethers".

SUMMARY OF THE INVENTION

The present invention resides in a fluorinated ether having the following formula:

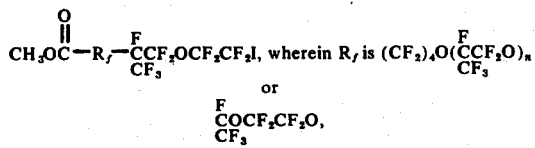

wherein $n$ is zero to 10, inclusive, preferably 1 to 5, inclusive.

In one process for preparing fluorinated ethers of this invention, an anhydrous alkali metal fluoride, e.g., potassium fluoride, and an omega-carbomethoxyperfluoroalkylether acid fluoride are initially mixed in a solvent. The mixture is usually stirred at ambient temperature for a period of about 0.5 to 3 hours. Thereafter, the mixture is cooled, e.g., in an ice bath, and iodine monochloride is added. Generally, a molar excess of the alkali metal fluoride is mixed with the acid fluoride, e.g., about 1.5 to 2 moles of alkali metal fluoride per mole of the acid fluoride. A molar excess of the iodine monochloride as compared to acid fluoride is preferably employed, e.g., about 1.5 to 5 moles of iodine monochloride per mole of acid fluoride.

After addition of the iodine monochloride as described in the preceding paragraph, the reactor containing the materials is pressurized, e.g., to 60 psi, with tetrafluoroethylene. A reaction occurs at ice temperature that is accompanied by a reduction in pressure. Additional tetrafluoroethylene is periodically added until there is substantially no pressure drop. After venting any excess tetrafluoroethylene, the reaction mixture is poured into water. After removing any excess iodine by a sodium thiosulfate wash, the reaction mixture is extracted with a fluorinated solvent. The fluorinated ether product is thereafter separated from the extracted reaction mixture by fractional distillation.

In another process for preparing a fluorinated ether of this invention, a perfluoroalkyl bis acid fluoride is utilized instead of the monoacid fluoride mentioned above. Also, except for the fact that the reaction is carried out in a 1:1 stoichiometry, the procedure inclusive of the addition of tetrafluoroethylene, as described above, is followed. Upon completion of the tetrafluoroethylene addition, excess tetrafluoroethylene and any low boiling volatile products are removed under vacuum. The remaining product is esterified with methanol to obtain the omega ester perfluoroalkylene ether iodide. Any excess iodine is then destroyed with a sodium thiosulfate wash. The organic layer is further extracted with a fluorinated solvent. The fluorinated ether is then recovered from the extracted mixture by fractional distillation.

The mono- and diacid fluorides used in synthesizing the fluorinated ethers of this invention can be prepared by following essentially the procedure described by C. G. Fritz et al in U.S. Pat. No. 3,114,778. Thus, a substituted perfluoroalkylether acid fluoride, $CH_3OC(O)(CF_2)_3COF$, is reacted with hexafluoropropylene epoxide in the presence of metal fluoride, such as potassium fluoride, to yield oligomeric products having the following formula:

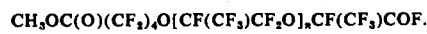

The oligomeric products can be separated by fractional distillation to provide a series of omega-carbomethoxyperfluoroalkylether acid fluorides in which $n$ can vary from zero to 10. Also, according to the disclosure of C. G. Fritz et al, a perfluoroacyldianion ($^{\ominus}OCF_2R_fCF_2O^{\ominus}$) is reacted with hexafluoropropylene epoxide in the presence of a metal halide to yield a perfluoroalkylether bis acid fluoride having the following formula:

As previously mentioned, the fluorinated ethers of this invention can be used as intermediates in synthesizing monomeric materials. Thus, the fluorinated ethers can be used in preparing diesters, diamides, dinitriles and diimidate esters following a four-stage procedure as represented by the following equations:

(I)

(II)

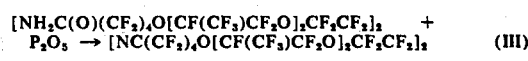
(III)

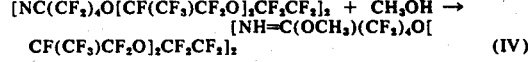
(IV)

As seen from the foregoing equations, in the first stage a representative omega-carbomethoxyperfluoroalkylene iodide of this invention is reacted with particulate zinc to form a diester. The reaction is carried out in acetic anhydride and trichlorotrifluoroethane under reflux conditions and in an inert atmosphere. In the second stage, ammonia is bubbled through an ether-1,1,2-trifluorotrichloroethane solution of the diester recovered from the first stage to form a diamide product. The diamide product recovered from the second stage is mixed and heated with phosphorous pentoxide in the third stage to provide the dinitrile. In the final and fourth stage, the dinitrile recovered from the third stage is added to a solution of sodium in methanol. In the reaction that occurs, the diimidate ester is obtained. It is to be understood that by following the same procedure other diimidate esters can be prepared from other fluorinated ethers of this invention as described hereinabove. For a more complete discussion of the preparation of the diimidate esters, reference may be had to commonly assigned application Ser. No. 610,520, filed on Sep. 4, 1975, by Christ Tamborski, a coinventor herein. This disclosure of that application is incorporated herein by reference.

The diimidate ester, synthesized as described above using the fluorinated ethers of this invention as starting materials, are useful as monomers in preparing thermally stable polymers. Thus, polycondensation of the diimidate esters with fluorocarbon ether bis(o-aminophenol) monomers provide linear fluorocarbon ether bibenzoxazole polymers. The polymers are elastomeric, have a very low glass transition temperature, and are oxidatively stable at elevated temperatures. The polycondensation reaction is usually carried out in hexafluoroisopropanol at about 50° to 55° C in the presence of four molar equivalents of glacial acetic acid.

Examples of fluorocarbon ether bis(o-aminophenol) monomers include 1,11bis(2-amino--hydroxyphenyl)perfluoro-3,9-(dioxaundecane, 1,14-bis(3amino-4-hydroxyphenyl)perfluoro-5,10-dimethyl-3,6,9,12-tetraoxatetradecane and 1,17-bis(3-amino-4-hydroxyphenyl)perfluoro-3,6,9,15-tetraoxaheptadecane. For a description of the preparation of these monomers, reference can be made to U.S. Pat. No. 3,846,376 and to application Ser. No. 610,470, of common assignee, filed on Sept. 4, 1975 now U.S. Pat. No. 4,005,142, by Robert C. Evers, both of which are incorporated herein by reference.

A more comprehensive understanding of the invention can be obtained by referring to the following illustrative examples which are not intended, however, to be unduly limitative of the invention.

EXAMPLE I

Tetraglyme solvent (100 ml) and anhydrous potassium fluroide (10 g; 0.16 mole) were charged into a Fisher-Porter pressure reactor and the vessel was evacuated. An omega-carbomethoxyperfluoroalkylether acid fluoride, $CH_3OC(O)(CF_2)_4OCF(CF_3)CF_2OCF(CF_3)COF$, (54 g; 0.091 mole) was added and the mixture was stirred at ambient temperature for one hour. The mixture was cooled in an ice bath and iodine monochloride (30 g; 0.18 mole) was added. The reactor was pressurized with tetrafluoroethylene to 60 psi. The reaction at ice temperature was followed by a reduction of pressure. Periodically, more tetrafluoroethylene was added until the pressure drop was insignificant. Excess tetrafluoroethylene was vented and the reaction mixture was poured into water. The excess iodine was removed by a sodium thiosulfate wash and the reaction mixture was extracted with trifluorotrichloroethane. Distillation produced 30.0 g (45.1% yield) of the desired compound $CH_3OC(O)(CF_2)_4O[CF(CF_3)CF_2O]_2CF_2CF_2I$, b.p. 90°–93° at 0.6 mm. The $^1H$ and $^{19}F$ nuclear magnetic resonance data and infrared data were consistent with the product's chemical structure. Mass spectral analysis, calculated $M^+$ 834 found $M^+$ 834 and elemental analysis were consistent with the above structure.

Analysis — Calc'd: C,20.14, H,0.36; Found: C,20.36, H,0.29.

EXAMPLE II

Tetraglyme solvent (220 ml) and anhydrous potassium fluoride (18 g; 0.3 mole) were charged into a Fisher-Porter pressure reactor and the vessel was evacuated. An omega-carbomethoxyperfluoroalkylether acid fluoride, $CH_2OC(O)(CF_2)_4[CF(CF_3)CF_2O]_2CF(CF_3)COF$, (145 g; 0.19 mole) was added and the mixture was stirred at ambient temperature for one hour. The mixture was cooled in an ice bath and iodine monochloride (28 g; 0.5 mole) was added. The reactor was pressurized with tetrafluoroethylene to 60 psi. The reaction at ice temperature was followed by a reduction of pressure. Periodically, more tetrafluoroethylene was added until the pressure drop was insignificant. Excess tetrafluoroethylene was vented and the reaction mixture was poured into water. The excess iodine was removed by a sodium thiosulfate wash and the reaction mixture was extracted with trifluorotrichloroethane. Distillation produced 82 g (50.8% yield) of the desired product $CH_3OC(O)(CF_2)_4O[CF(CF_3)CF_2O]_3CF_2CF_2I$, b.p. 102°–104° at 0.4 mm. The $^1H$ and $^{19}F$ nuclear magnetic resonance data and infrared data were consistent with the product's chemical structure. Mass spectral analysis, calculated $M^+$ 1000 found $M^+$ 1000 and elemental analysis were consistent with the above structure.

Analysis — Calc'd: C,20.40, H,0.30; Found: C,20.54, H,0.10.

EXAMPLE III

Tetraglyme solvent (110 ml) and anhydrous potassium fluoride (8.7 g; 0.15 mole) were charged into a Fisher-Porter pressure reactor and the vessel was evacuated. A perfluoroalkylether bis acid fluoride, $FCOCF(CF_3)OCF_2CF_2OCF(CF_3)COF$, (73 g; 0.17 mole) was added and the mixture was stirred at ambient temperature for one hour. The mixture was cooled in an ice bath and iodine monochloride (25 g; 0.15 mole) was added. The reactor was pressurized with tetrafluoroethylene at 60 psi. The reaction at ice temperature was followed by a reduction in pressure. Periodically, more tetrafluoroethylene was added until the pressure drop was insignificant. Excess tetrafluoroethylene and the low boiling volatile products, mostly starting bis acid fluoride, were removed under vacuum. The remaining product was esterified with methanol and the excess iodine destroyed by a sodium thiosulfate wash. The organic layer was further washed with water and extracted with trifluorotrichloroethane, and dried (MgSO$_4$). GLC analysis of the reaction mixture indicated the following three products:

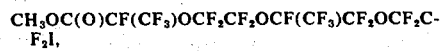

ICF$_2$CF$_2$OCF$_2$(CF$_3$)CFOCF$_2$CF$_2$OCF(CF$_3$)CF$_2$OCF$_2$CF$_2$I, and

CH$_3$OCOCF(CF$_3$)OCF$_2$CF$_2$OCF(CF$_3$)OCOCH$_3$.

Fractional distillation of the mixture produced the iodo-ester CH$_3$OC(O)CF(CF$_3$)OCF$_2$CF$_2$OCF(CF$_3$)CF$_2$OCF$_2$CF$_2$I, b.p. 101°–102° to 12 mm (50.7% yield). The $^1$H and $^{19}$F nuclear magnetic resonance data and infrared data were consistent with the product's chemical structure. Mass spectral analysis, calculated M$^+$ 684 found M$^+$ 684 and elemental analysis were consistent with the above structure.

Analysis — Calc'd: C,19.30; H,0.44; Found: C,19.26; H,0.29.

As seen from the foregoing, the present invention provides fluorinated ethers having two functional end groups. Because of these two reactive sites, the compounds are useful as precursors for monomers that can be used in polymerization reactions.

As will be evident to those skilled in the art, modifications of the present invention can be made without departing from the spirit and scope of the invention.

We claim:

1. Fluorinated ethers having the following formula:

, wherein R$_f$ is

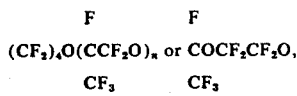

where $n$ is zero to 10, inclusive.

2. The composition according to claim 1 in which $n$ is 1 to 5 inclusive.

3. The composition according to claim 1 in which R$_f$ is

where $n$ is 1 to 5, inclusive.

4. The composition according to claim 1 in which R$_f$ is

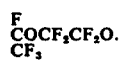

* * * * *